US006752962B2

(12) United States Patent
Carr et al.

(10) Patent No.: US 6,752,962 B2
(45) Date of Patent: *Jun. 22, 2004

(54) MINIATURIZED INTEGRATED SENSOR PLATFORM

(75) Inventors: Richard A. Carr, Rowlett, TX (US); Jose L. Melendez, Plano, TX (US); Kirk S. Laney, Plano, TX (US)

(73) Assignee: Texas Instruments Incorporated, Dallas, TX (US)

( * ) Notice: Subject to any disclaimer, the term of this patent is extended or adjusted under 35 U.S.C. 154(b) by 41 days.

This patent is subject to a terminal disclaimer.

(21) Appl. No.: 10/007,159

(22) Filed: Dec. 4, 2001

(65) Prior Publication Data

US 2002/0123152 A1 Sep. 5, 2002

Related U.S. Application Data

(60) Continuation of application No. 09/429,036, filed on Oct. 29, 1999, now Pat. No. 6,326,210, which is a division of application No. 08/942,089, filed on Oct. 1, 1997, now Pat. No. 6,045,756.
(60) Provisional application No. 60/027,226, filed on Oct. 1, 1996.

(51) Int. Cl.[7] .................. G01N 21/47; G01N 21/01; G01N 21/75; G01N 21/17; G01N 21/27
(52) U.S. Cl. .................. 422/82.05; 422/50; 422/55; 422/57; 422/58; 422/82.07; 422/82.08; 422/82.09; 422/82.11; 422/83; 436/164; 436/165; 436/171; 436/518; 29/407.04; 29/592; 29/720; 29/709; 29/833
(58) Field of Search ............... 422/50, 55, 57, 422/58, 82.05, 82.07, 82.09, 82.11, 83; 436/164, 165, 171, 518; 29/407.04, 592, 720, 709, 833

(56) References Cited

U.S. PATENT DOCUMENTS

| 4,618,771 | A |   | 10/1986 | Farren ................... 250/343 |
| 4,857,273 | A | * | 8/1989  | Stewart ................. 422/82.11 |
| 5,439,647 | A |   | 8/1995  | Saini ................... 422/82.11 |
| 5,447,845 | A |   | 9/1995  | Chu et al. ................ 435/6 |
| 5,517,313 | A |   | 5/1996  | Colvin, Jr. ............... 356/417 |
| 5,640,234 | A | * | 6/1997  | Roth et al. ............... 356/128 |
| 5,650,123 | A |   | 7/1997  | Saini et al. ............. 422/82.11 |
| 6,045,756 | A | * | 4/2000  | Carr et al. ............. 422/82.11 |
| 6,326,210 | B1 | * | 12/2001 | Carr et al. ............... 436/164 |

* cited by examiner

Primary Examiner—Jill Warden
Assistant Examiner—Brian Sines
(74) Attorney, Agent, or Firm—David Denker; Wade James Brady, III; Frederick J. Telecky, Jr.

(57) ABSTRACT

A miniaturized integrated sensor (50) useful for indicating the presence of a sample analyte is disclosed. The sensor (50) has a platform (52) with an upper surface (53) and a detector (62), light source (60), waveguide (58), and reflective fixtures (60, 62) embedded in the platform (52). The light source (60) is preferably a light emitting diode and sits in a cup-shaped dimple (68) that directs light from the light source (60) toward one of the reflective fixtures (64) to uniformly distribute light across the waveguide (58). The waveguide (58) is coupled to an upper surface (53) of the sensor platform (52) and is coated with a thin film of indicator chemistry (70) which interacts with the sample analyte to produce optic signal changes that are measurable by the detector (62). A lead frame (51) in the platform (52) has pins (54, 55, 56) which provide the interface to the outside world. In one embodiment, sensor package (100) has a unique shape that requires a predetermined insertion and removal into an instrument harness or other similar application.

16 Claims, 2 Drawing Sheets

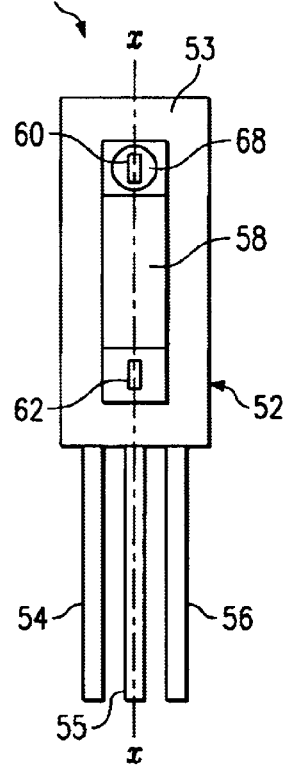
FIG. 1 (PRIOR ART)
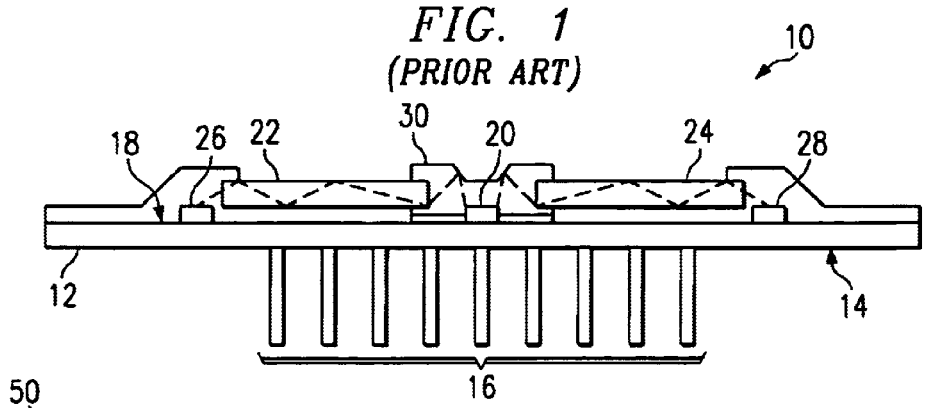
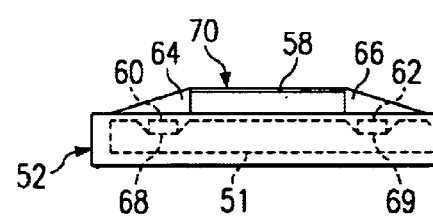
FIG. 3
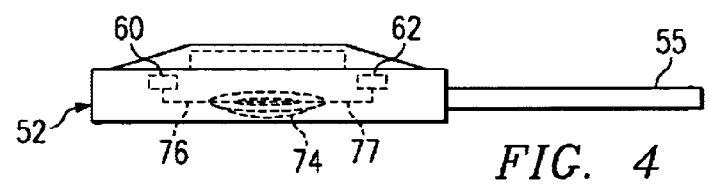
FIG. 4
FIG. 2
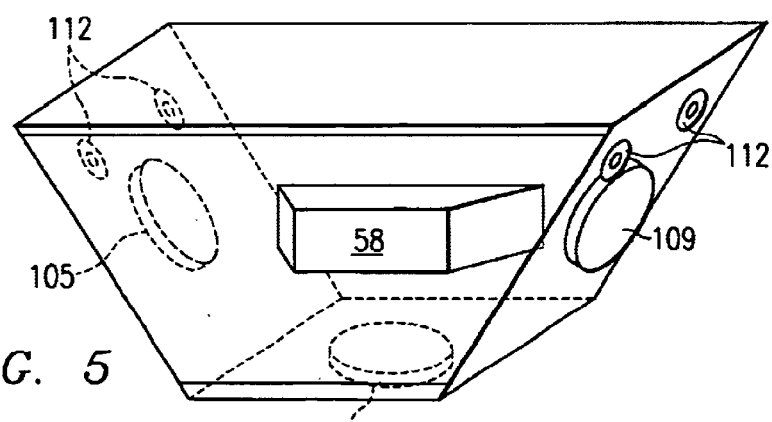
FIG. 5

MINIATURIZED INTEGRATED SENSOR PLATFORM

This application is a continuation of Appl. No. 09/429,036, filed Oct. 29, 1999, now U.S. Pat. No. 6,326,210, which is a divisional of Appl. No. 08/942,089, filed Oct. 1, 1997, now patent 6,045,756, which claims priority from Appl. No. 60/027,226, filed Oct. 1, 1996.

TECHNICAL FIELD

The present invention relates in general to the field of (bio)chemical sensors and more specifically to a miniaturized integrated sensor platform suitable for use as an optic-based sensoring device.

BACKGROUND OF THE INVENTION

Without limiting the scope of the invention, its background is described in connection with a (bio)chemical sensor wherein a thin film, fiber or other article is chemically treated with a substance known to interact in the presence of a second substance so as to produce a reaction which can be detected and quantified by analytical methods.

(Bio)chemical sensor systems have been developed and used in the fields of chemical, biochemical, biological or biomedical analysis, process control, pollution detection and control and other areas. A typical application involves the chemical coating of a thin film, cable or other article followed by excitation and measurement in the presence of the particular sample of interest. Recent advances in miniaturized sensor technology have resulted in three popular configurations: fluorescence-based, surface plasmon resonance, and light transmission sensors.

A known prior art sensor system is the fluorescence-based fiber optic oxygen cable sensor which uses a single high brightness Light Emitting Diode (LED)to produce an excitation signal that catalyzes the emission properties of the fluorescence coating material. The excitation signal is first guided through a filter and then through the cable, which is coated, unclad, and mounted in a gas flow cell. Light escaping the cell excites the coated dye on the cable which, in turn, emits a certain intensity of light related to the concentration of the oxygen sample. The emitted light is then directed through a second filter and to a light detector via a collecting lens. The output of the detector is amplified and read out on an instrument.

Another known prior art sensor system uses a multi-pin hermetically sealed package that encloses all of the light filtering, light guiding and light detection components within. The package can be inserted into a socket or slot of a computer or other system processor creating an interface between the sensor and the processor via the pins. Due to the number of pins, however, replacing, removing or inserting the chip may be difficult or require special tools.

Prior art sensor systems have limited use in most practical field applications. The signal generator, LED, lens, filter, detector, amplifier and other components are bulky, require significant amounts of work space and cannot be easily transported to the sample site. The costs of manufacturing and maintaining such systems are high prohibiting high volume manufacturing.

Moreover, prior art sensors are not designed for low cost disposable applications wherein the sensor can be disposed after serving its useful life. A cost effective sensor having an onboard power cell has not been contemplated and, as such, prior art sensor packages require an interface to an external power supply or other source of operating power.

Another limitation of the prior art sensors the number and types of components used which in many instances are custom made based on the particular application. System maintenance is high and requires specialized knowledge.

Yet another limitation of the prior art sensors is system integration with equipment such as a personal computers, hand held instruments or other signal processors used to measure and quantify sample data. A dedicated bus or interface between the sensor and the processor is required increasing the number of signal paths between the sensors detector and the processor.

SUMMARY OF THE INVENTION

Prior art sensors can not be used in most disposable and field use applications. The recent availability of low cost high intensity light sources and miniaturized detector components, however, permits the design of a more compact and miniaturized sensor platform. A miniaturized sensor would provide many advantages over the bulkier prior art sensor systems which are better suited for laboratory and research applications.

As such, it is a primary object of the present invention to provide a miniaturized integrated sensor capable of use in optically guided sensing applications. The sensor package of the present invention integrates a light source, detector means, light guide optics and a simplified system interface into a compact miniaturized package. In one embodiment, the package incorporates an onboard power source, such as a lithium cell battery of the type readily available in industry, giving the sensor a useful lifetime equal to that of the power source. Thus, a fully operable sensor is disclosed that can be easily replaced and discarded after use.

Another object of the present invention is to provide a miniaturized sensor with a simplified interface to external systems such as computers, signal processors, and other similar processors which perform analytical processing of the output from the sensor's light detector. In one embodiment, the sensor package has a three-pin lead frame extending from the platform with signal conduits to power, ground and the detector output. In a second embodiment, a two-pin version is provided wherein the onboard power source eliminates the need for a third signal interface.

Yet another object of the present invention is to provide a sensor with a uniquely shaped package which fits securely into an opening or mounting harness in a hand held instrument, computer or other similar fixture. In one embodiment, the sensor housing is shaped and sized to fit a fixture in a hand held application specific instrument which uses the sample data from the sensor to perform further signal processing and analytical functions. Surface contacts on the sensor walls provide the interface with the instrument. Since the device is uniquely shaped it fits into the mounting harness about a predetermined position allowing simple insertion and removal.

Disclosed in one embodiment of the invention, is an integrated sensor for detecting the presence of one or more specific material samples of interest having a platform to which a light source, detector, waveguide and reflective pyramidal structures are affixed to form a miniaturized fully integrated sensor package. A three-pin lead frame extends from the sensor package providing the interface between the sensor and an external processor. In another embodiment, surface contacts provide the same function. Power can be external or provided internally by a self contained battery cell which is coupled to the platform and the various active components of the sensor. In yet another embodiment, the package is uniquely shaped and sized requiring a unique placement within a mounting harness in a computer, hand held instrument, wall mount harness or other similar fixture.

For a more complete understanding of the present invention, including its features and advantages, reference is now made to the following detailed description, taken in conjunction with the accompanying drawings.

BRIEF DESCRIPTION OF THE DRAWINGS

In the drawings:

FIG. 1 depicts a prior art sensor platform;

FIG. 2 is a top side view of a miniaturized integrated sensor package according to one embodiment of the invention;

FIG. 3 is a cross sectional view of the sensor package of FIG. 2;

FIG. 4 is an alternative embodiment of a sensor package according to the invention;

FIG. 5 illustrates the internal arrangement of sensor components for the sensor package of FIG. 4;

Corresponding numerals and symbols in the different figures refer to corresponding parts unless otherwise indicated.

DETAILED DESCRIPTION OF THE PREFERRED EMBODIMENT

Figure 6:
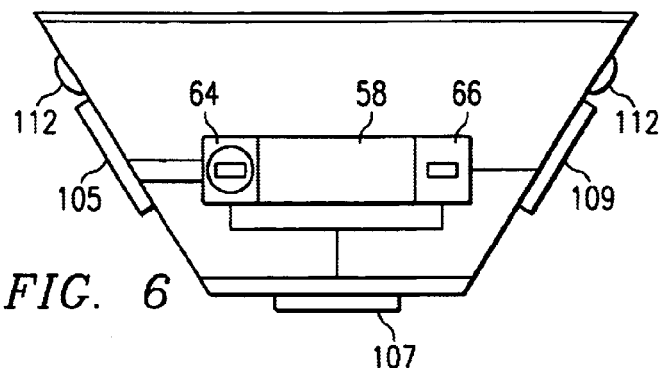
FIG. 6 is a side profile view of an miniaturized sensor package having an internal power source according to the invention.

Referring now to FIG. 1, a prior art sensor is shown and denoted generally as 10. Sensor 10 is used in biochemical sensing application to detect the presence of a given sample gas, liquid or compound by detecting optical changes produced by the molecular interaction between a thin layer of biochemistry coat and the particular sample of interest. The chemistry is chosen for its interactive properties in the presence of the sample and, as such, the sensor 10 has widespread application depending on the particular chemistry/sample combination of interest. Suitable combinations chemistry/sample combinations include chloride/oxygen, hydroxypyreneprisulphonic acid/carbon dioxide sample, octadecyl fluorescein/nitrate and acetic acid/alcohols. Other combinations are numerous and well known in the art.

As illustrated in FIG. 1, sensor 10 has a platform 12 to which the various sensor components are affixed. The platform 12 is made of a suitable substrate material and in some embodiments has a light absorbent quality that acts to eliminate scattered light. Coupled to the bottom surface 14 of the platform 12 are pins 16 which provide the signal interface between the sensor 10 and other remote processing systems (not shown). In this way, the sensor 10 receives power and communicates with the outside world.

Affixed to the upper surface 18 of the platform 12 are the various sensor components including light source 20, waveguides 22 and 24, and detectors 26 and 28. The specific device embodiments of these components vary depending on application although for miniaturized sensor some devices are preferred. For example, it is common for light source 20 to be a single high brightness light emitting diode (LED) of the type commonly available in industry. A light-to-voltage sensor, such as the TSL250, can be a suitable device component for detectors 26 and 28, although other detector component may also be used.

Waveguide 24 is chemically coated depending on the sample of interest and either molded as part of the sensor package or attached later depending on application and specific chemistry. Waveguide 22 is untreated or partially untreated providing a base point for signal referencing. In operation, the light source 20 generates an output signal with a wavelength characteristic that interacts with the coating material. The output signal from light source 20 is first directed by cast 30 into each waveguide 22, 24, which are made of a light transmissive material, where it reflects internally off the corresponding waveguide surface and towards the detectors 26, 28.

When a given sample, i.e., oxygen, carbon dioxide, nitrate, alcohols and others, comes in contact with the waveguide 24 surface, the chemical coat thereon changes its optical properties so that the total light incident on the detector 28 is measurably altered. As known and appreciated by those skilled in the art, the excitation signal from light source 20 interacts with the chemical coat which, in turn, interacts with the sample of interest to alter the total light transmitted through the waveguide 24 related to the sample concentration. A portion of this transmitted light is gathered by sensing surface of the detectors 28 and amplified to create a voltage swing indicative of the sample's presence.

The output signals from the detectors 26 and 28 can be compared to provide a differential output. This output is accessed through interface 16 and analyzed by a remote processing system wherein analytical derivation is performed and meaningful information regarding the sample is obtained.

FIG. 1 illustrates a prior art sensor system having a light transmission device configurations wherein a light wavelength is directed across one or more treated waveguide members (26, 28). It should be understood, however, that other platform types and arrangements may be employed or exist in the prior art and, as such, it is intended that principles and advantages of the present invention apply without limitation to all such configurations. For example, the present invention may have application in the fields of surface plasmon resonance and fluorescence based sensors. In this regard, reference is made to the following wherein the operating and functional aspects of such devices are discussed: Ralph C. Jorgensen, Chuck Jung, Sinclair S. Yee, and Lloyd W. Burgess, *Multi-wavelength surface plasmon resonance as an optical sensor for characterizing the complex refractive indices of chemical samples*, Sensors and Actuators B, 13–14, pp. 721–722, 1993; B. D. McCraith, G. O'Keeffe, C. McDonoagh, and A. K. McEvoy, *LED based fiber optic oxygen sensor using sof-gel coating*, Electronic Letters, Vol. 30, No. 11, pp. 888–889, May 26, 1994.

Turning now to FIGS. 2 and 3, the advantages of the present invention over the prior art sensor platforms are illustrated and made apparent to those skilled in the art. FIGS. 2 and 3 depict an alternative sensor package for a miniaturized (bio)chemical sensor having a reduced pin count and significant size advantages over the prior art. Specifically, FIG. 2 shows a top side view of a miniaturized sensor 50 in accordance with one embodiment of the invention. FIG. 3 is a cross sectional view of sensor 50 taken along line X.

Sensor 50 has a platform 52 which forms a substantially rectangular box shaped housing for the various sensor components. The platform 52 can be made of a plastic, hard resin material, epoxy substance or similar substrate material and may be molded or pre-shaped from a cast die providing a low cost and easy to manufacture device.

A lead frame 51 has pins 54, 55 and 56 which extends outward from the platform 52 and provide the interface to the outside world. In one embodiment, pins 54, 55 and 56 correspond to ground, power and output, respectively.

Coupled to the sensor platform 52 is waveguide 58 which extends along a substantial portion of upper surface 53 of platform 52. Waveguide 58 is made of a light transmissive material such as glass, a ceramic substrate, clear plastic or similar material. A light source 60 and detector 62 are embedded in the platform 52 substrate about opposite extremities of the waveguide 58. Triangular shaped reflecting fixtures 64 and 66 are coupled to opposite ends of the waveguide 58 and also to upper surface 53 of the platform 58.

Fixtures 64 and 66 work to direct the light energy from the light source 60 to detector 62 via waveguide 58. The placement of fixture 64 above light source 60 and fixture 66 above detector 62 helps achieve a uniform dispersion of light across the waveguide surface thereby improving the coupling characteristics of light from the light source 60 to the detector 62. It should be understood, however, that other coupling means may be devised and are within the scope of the present invention.

Light source 60 is centrally configured inside dimple 68 which forms a substantially cup-shaped reflective bevel underlying light source 60 and serves two primary purposes. First, dimple 68 directs light from light source 60 to fixture 64 which in turn reflects and distributes the light more evenly along the coated surface 70 on waveguide 58. Second, dimple 68 minimizes the amount of light from the light source 60 that reaches the detector 62 directly, without having interacted with the coated surface 70.

Likewise, the detector 62 sits inside dimple 69. In the preferred embodiments, dimples 68 and 69 are stamped in the lead frame 51 during manufacture thus limiting the number of separate parts.

As shown, the detector 62 is centrally placed in an underlying fashion about reflecting fixture 66 giving the detector 62 a uniform area of light reception that increases sensitivity to light emissions from coated surface 70.

Figure 8:
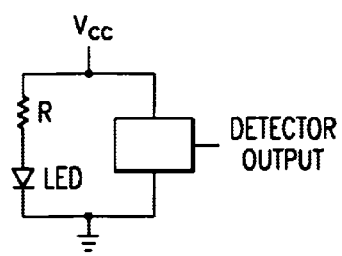
FIG. 8 shows a circuit diagram for an integrated sensor.

Thus, a complete sensor is disclosed having a light source 60, detector 62 and waveguide 58 components among others. The components are operably coupled to each other in a manner known to those skilled in the art according to the invention. For example, without limiting the invention, the circuit diagram of FIG. 8 demonstrates one possible arrangement of the components according invention.

In general, the light source 60 is implemented as a series combination of a light emitting diode LED and a limiting resistor R. A photo diode amplifier chip, such as the Texas Instruments, Inc. TSL250, is a suitable device for this purpose. Power level Vcc and a reference GND are two inputs of the package lead frame while the detector output comprises a third pin. A two-pin embodiment is also envisioned wherein an internal power source, such as a Lithium cell or charged cell capacitor, is included eliminating the third pin to the sensor 50. This configuration is illustrated in FIG. 4 wherein power source 74 is embedded in the platform 52 and interfaced to the light source 60 via lead 76 and to the detector 62 via lead 77. Other arrangements may be obtained all within the scope of the invention.

As illustrated by FIGS. 2, 3 and 4, a primary advantage of sensor 50 over prior art devices is its small size, miniaturized dimensions and small lead count. The sensor package can be manufactured according to existing platform standards, such as the TSL250 light-to-voltage optical sensor of Texas Instruments, Inc. which combines a photo diode/amplifier in a clear plastic three-pin package having an active area of approximately 1.0 $mm^2$. Other package types and dimensions are also envisioned and within the scope of the present invention.

In the preferred embodiment, a coated surface 70 on the waveguide 58 forms a thin film of an absorbing chemistry chosen for how it interacts with the sample of interest to produce a detectable signal change. The properties of chemical coat 70 are well known in the art. For example, in one embodiment an indicator is embedded in a matrix such as a polymer or a sol-gel and deposited on the waveguide 58. Examples of such indicators and the corresponding sample analyte are listed below:

| INDICATOR | ANALYTE | WAVELENGTH |
| --- | --- | --- |
| Magon | Magnesium | 520 mn |
| Pyrogallol red-molybdate | Total Protein | 600 nm |
| Brilliant blue G. (Coomassie blue) | Total Protein | 595 nm |
| Ferrozine | Iron | 560 nm |
| Picric acid | Creatinine | 500 nm |
| Arsenazo III | Calcium | 600 nm |
| Bromcresol | Albumin | 628 nm |

Turning now to FIG. 5, an alternative package configuration for a miniaturized integrated sensor in accordance with the invention is shown and denoted as 100. The package 100 has surface contacts 105, 107 and 109 which extend from three substantially noncoplanar walls of the package 100 and form a trapezoidal shaped structure. The shape and arrangement of the package 100 ensure unique insertion of the sensor within a mounting harness or other fixture where the sensor is inserted or removed from.

Contacts 105, 107 and 109 provide conductive pathways to the internal device electronics and other components as illustrated in the above circuit diagram and in FIG. 6. The waveguide 58 occupies a portion of at least one surface of the package 100 and has the thin layer of chemical coating thereon. The waveguide 58 can be integrally molded on the package or attached separately depending on the chemical coat and design.

Figure 7:
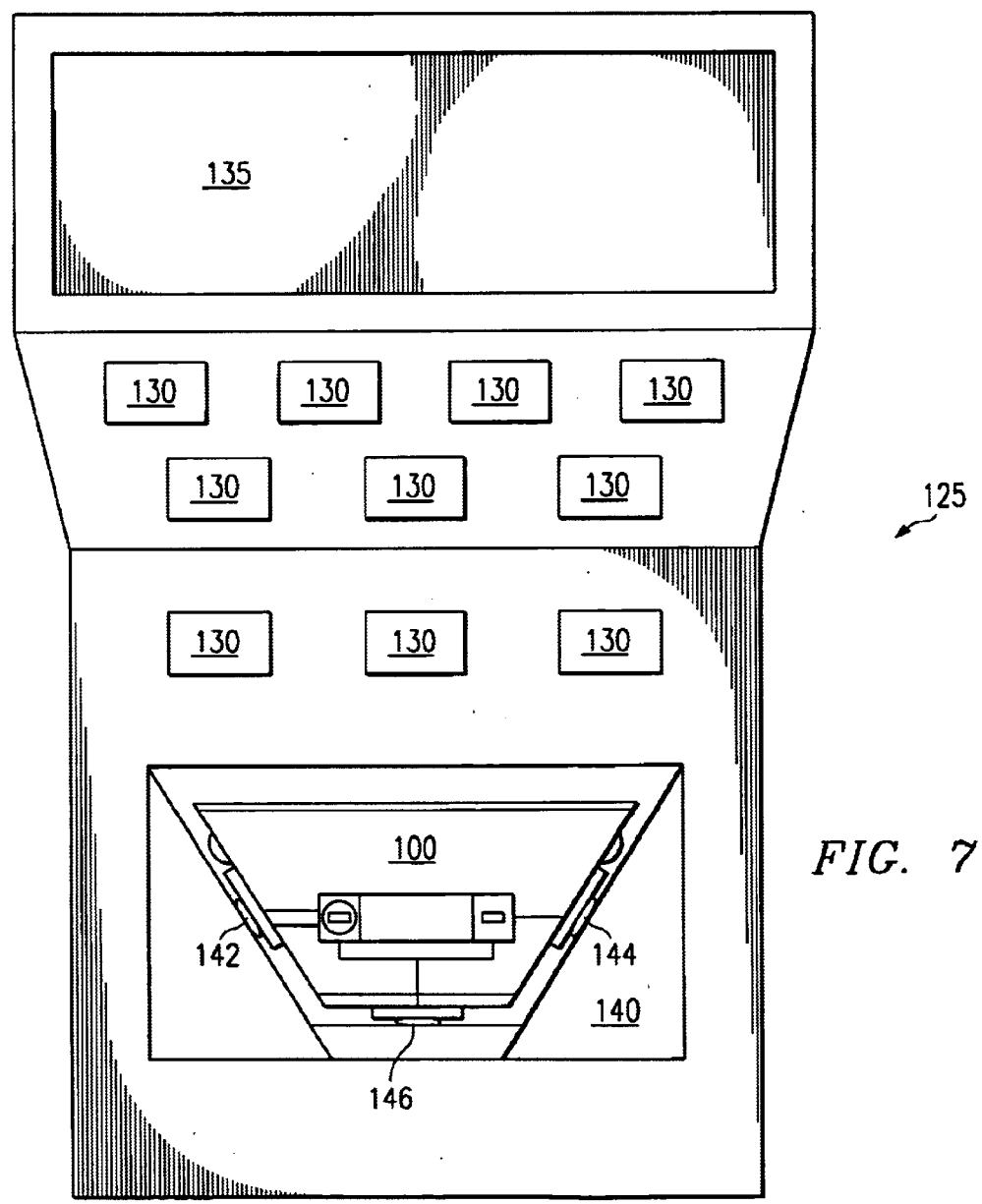
FIG. 7 shows use of a miniaturized integrated sensor in and easy to install and remove instrument application.

A principle advantage of the package 100 is the shape which requires unique placement in a predetermined orientation into a mounting harness or similar opening in a hand held application specific instrument. An application of such a use is illustrated in FIG. 7. Snap-in insertion and removal of the package 100 is facilitated by locks 112 which can be placed on a package surface to lock the device in place.

The short length of the contacts 105, 107 and 109 makes the package 100 ideal for disposable applications since it can be easily inserted and removed by the user.

It should be understood, however, that the invention encompasses more than the trapezoidal shaped housing of FIGS. 5 and 6, and that the invention may be practiced using a plurality of package configurations all of which restrict and define the placement of the sensor within a mount, harness or instrument panel.

In FIG. 7, use of the package 100 in a hand held instrument 125 is illustrated. The size, weight and construction of instrument 125 makes it ideal for field use near the sample of interest. Controls 130 give access to various functions and commands depending on the application and nature of the instrument 125. For example, the instrument can be used to detect hazardous substances at a given location or the smoke content in the air. Other uses are also envisioned.

A screen display 135 provides visual feedback information concerning the sample and can be used to view results and other data.

The instrument harness 140 is provided to secure the sensor package 100 within instrument 125. As shown, the harness 140 has been shaped and sized to accommodate the package 100, although many configurations of the harness 140 are embodied by the invention. Since the harness 140 is shaped to fit the sensor package 100, the user is required to place the sensor in a predetermined orientation within the harness 140.

The harness 140 includes three mating contacts 142, 144 and 146 which interface with surface contacts 105, 107 and 109 of sensor packages 100 respectively to provide a communications pathway between the detector 62 and the instrument 125. This establishes the signals paths for power, reference and the detector output.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. An integrated biochemical sensor package comprising:
   a platform;
   a waveguide having an upper surface affixed to said platform, said waveguide having a thin layer of chemical coating affixed on said upper surface;
   first and second reflective fixtures coupled to opposite extremes of said waveguide and touching said platform,
   a light source within said package, said light source arranged to emit light towards said first reflective fixture; and
   a detector within said package and near second reflective fixture.

2. The integrated biochemical sensor package according to claim 1 further comprising:
   a lead frame extending from said platform on a place parallel to said thin layer of coating;
   a first dimple underlying said first reflective fixture;
   said light source embedded in said first dimple and arranged to emit light outward towards said first reflective fixture.

3. The integrated biochemical sensor package according to claim 1 wherein said waveguide is made of a light transmissive material.

4. The integrated biochemical sensor package according to claim 2 wherein said lead frame has three pins extending outward from said platform.

5. The integrated biochemical sensor package according to claim 1 wherein said light source is a series combination of a diode and resistor.

6. The integrated biochemical sensor package according to claim 1 wherein said detector is an photo diode amplifier chip.

7. The integrated biochemical sensor package according to claim 1 wherein said light source is a single high intensity light emitting diode.

8. The integrated biochemical sensor package according to claim 1 wherein said platform forms a substantially rectangular shaped enclosure for housing various sensor components.

9. The integrated biochemical sensor package according to claim 1 wherein said platform has a substantially trapezoidal shape.

10. The integrated biochemical sensor package according to claim 1 wherein said waveguide is integrally molded on said platform.

11. The integrated biochemical sensor package according to claim 2 further comprising a second dimple underlying said second reflective fixture wherein said detector sits inside said second dimple.

12. A miniaturized integrated biochemical sensor for indicating the presence of a given sample based comprising:
    a sensor platform having a substantially rectangular box shape form, said platform having a substantially flat upper surface and at least one end;
    a waveguide coupled to said upper surface of said platform, said waveguide having a first end and a second end opposite from one another;
    a first reflective fixture coupled to said first end of said waveguide and touching said upper surface of said platform;
    a second reflective fixture coupled to said second end of said waveguide and touching said upper surface of said platform;
    a light source embedded in said platform under said first reflective fixture; and
    a detector embedded in said platform opposite said light source about said one end of said platform and underlying said second reflective fixture.

13. The miniaturized integrated biochemical sensor of claim 12 wherein said light source is a light emitting diode.

14. The miniaturized integrated biochemical sensor of claim 12 further comprising:
    a three-pin lead frame extending from said one end of said platform; and
    a first dimple forming a substantially cup-shaped area on one pin of said lead frame and surrounding said light source under said first reflective fixture.

15. The miniaturized integrated biochemical sensor of claim 12 wherein a thin layer of chemical coating is deposited on said waveguide.

16. A sensor package suitable for biochemical sensing applications comprising:
    a substantially rectangular device platform;
    a light transmissive waveguide coupled to an upper surface of said platform and a surface with an indicator chemistry coat deposited thereon;
    first and second reflective fixtures coupled to opposite ends of said waveguide about said platform;
    a lead frame embedded in said platform and having a plurality of pins extending out from one end of said platform, said lead frame having a first dimple underlying said first reflective fixture and a second dimple underlying said second reflective fixture;
    a light source sitting in said first dimple under said first reflective fixture; and
    a detector sitting in said second dimple under said second reflective fixture, said detector means configured about said platform to optically receive light from said light source via said first reflective fixture through said waveguide and then through said second reflective fixture.

* * * * *